United States Patent
Lersch et al.

(10) Patent No.: US 7,226,584 B2
(45) Date of Patent: Jun. 5, 2007

(54) PREPARATIONS WITH DEODORIZING ACTION COMPRISING THE ZINC SALT OF RICINOLEIC ACID AND AT LEAST ONE AMINO FUNCTIONAL AMINE ACID

(75) Inventors: Peter Lersch, Dinslaken (DE); Felix Müller, Velbert (DE); Jörg Peggau, Essen (DE); Patrick Ulrich, Essen (DE)

(73) Assignee: Goldschmidt GmbH, Essen (DE)

( * ) Notice: Subject to any disclaimer, the term of this patent is extended or adjusted under 35 U.S.C. 154(b) by 548 days.

(21) Appl. No.: 10/309,432

(22) Filed: Dec. 4, 2002

(65) Prior Publication Data

US 2003/0133892 A1 Jul. 17, 2003

(30) Foreign Application Priority Data

Dec. 12, 2001 (DE) ................ 101 60 933

(51) Int. Cl.
  *A61Q 15/00* (2006.01)
  *A61Q 19/00* (2006.01)
  *A61K 8/00* (2006.01)
  *A61K 8/02* (2006.01)

(52) U.S. Cl. ............. 424/65; 424/66; 424/400; 424/401; 514/937; 514/938

(58) Field of Classification Search ............ 424/65, 424/400, 401, 67, 66, 68; 514/937, 938
See application file for complete search history.

(56) References Cited

U.S. PATENT DOCUMENTS 6,171,581 B1 * 1/2001 Joshi et al. ............. 424/65
6,534,046 B1 * 3/2003 Golz-Berner et al. ......... 424/65

FOREIGN PATENT DOCUMENTS

| DE | 1792074 | 10/1971 |
|---|---|---|
| DE | 37 26 636 C1 | 10/1988 |
| DE | 38 08 114 A1 | 9/1989 |
| DE | 40 14 055 A1 | 11/1991 |
| DE | 40 14 055 C2 | 11/1991 |

OTHER PUBLICATIONS

Klinische Erafahrungen mit topisch appliziertem L-Arginin, (200) Wohrab J. Marsch W. Ch, (pp. 485-486).

* cited by examiner

*Primary Examiner*—Shelley A. Dodson
(74) *Attorney, Agent, or Firm*—Scully, Scott, Murphy & Presser, P.C.

(57) ABSTRACT

Preparations with deodorizing action are provided. The preparations include the zinc salt of ricinoleic acid; amino-functional amino acids; solubility promoters; organic and/or inorganic acids; and, optionally, water.

9 Claims, No Drawings

PREPARATIONS WITH DEODORIZING ACTION COMPRISING THE ZINC SALT OF RICINOLEIC ACID AND AT LEAST ONE AMINO FUNCTIONAL AMINE ACID

FIELD OF THE INVENTION

The present invention relates to preparations with deodorizing action, and more particularly to deodorizing preparations which comprise the zinc salt of ricinoleic acid and at least one amino-functional amino acid, salt and/or derivative thereof.

BACKGROUND OF THE INVENTION

The formation of perspiration is a normal and healthy bodily function. Perspiration, in itself, is odorless. However, the degradation of the protein compounds present in perspiration by natural, Gram-positive skin bacteria produces body odor, which in today's society is typically perceived as overpowering, repulsive and neglectful. For this reason, a large number of cosmetic products have been developed for bodycare with the aim of eliminating this unpleasant odor of perspiration. Application forms of such products, which include both odor-inhibiting deodorants and also perspiration-inhibiting antiperspirants, comprise sticks, creams, soaps, roll-ons, as well as aerosols and pump sprays.

There are various active principles which are useful in these standard commercial cosmetic formulations. For example, deodorants conceal the unpleasant odors through the addition of perfumes. Usually, deodorants also comprise antimicrobial active ingredients such as Triclosan®, ethereal oils or Farnesol®. Such materials act as bactericides or bacteriostats to reduce the natural bacterial flora on the skin, thus preventing the formation of odor. A further possibility is the use of antiperspirants, which reduce the perspiration secretion. The active ingredients used are aluminum and zirconium salts which, due to their protein-precipitating nature, narrow the sweat glands and thus reduce the formation of perspiration. Likewise prior art deodorant products also include enzyme blockers, such as triethyl citrate, which intervene in the enzymatic mechanism of bacterial decomposition of perspiration by preventing the formation of unpleasant-smelling degradation products by deactivating the ester-cleaving lipases.

Furthermore, so-called odor absorbers are also known. Odor absorbers are substances which can chemically or physically bond the odor-forming compounds by adsorption or absorption, respectively. One representative of such odor absorber material is zinc salts of ricinoleic acid, the preparation of which is described in DE-B-17 92 074.

The patent literature also includes descriptions in which these zinc salts are used in combinations with zinc salts of abietic acid or with zinc salts of other saturated or unsaturated hydroxylated fatty acids having 16 or more carbon atoms, and other active ingredients listed above.

Zinc ricinoleate can chemically bond odor-intensive organic substances with sulfur- or nitrogen-containing functional groups, such as, for example, mercaptans, thioethers, low molecular weight carboxylic acids, such as isovaleric acid, as well as amines. A particular advantage of this type of odor removal is that the bacterial equilibrium of the skin flora is not adversely affected as a result.

The ability of zinc ricinoleate to chemically firmly bond substances of this type permits zinc ricinoleate to be used in industrial areas of application for reducing unpleasant domestic and industrial odors.

However, due to its polymeric salt structure, zinc ricinoleate can only be used directly to a limited degree. Zinc ricinoleate is a compound which is only sparingly soluble in customary cosmetic solvents. In order to obtain effective preparations, zinc ricinoleate must be used in combination with solvents and solubility promoters. The typical solvents used are mono- or polyhydric alcohols, optionally with the addition of water. Customarily used highly ethoxylated solubility promoters are unable, even in high concentrations, to keep the zinc ricinoleate in solution by themselves and flowable products are also not obtained as a result.

Examples of special solubility promoters for zinc ricinoleate can be found in the patent literature. For example, patent specification DE-B-37 26 636 describes deodorants based on zinc ricinoleate with solvents and solubility promoters, where the solubility promoters used are the hydrolyzed ene adducts of ricinic fatty acids and maleic anhydride.

Patent specification DE-B-38 08 114 likewise describes deodorants based on zinc ricinoleate with solvent and solubility promoters. The solubility promoters used in this prior art reference are partial esters of di- or polyhydroxyalkanes, mono- and disaccharides, polyethylene glycols or alkanolamines with the ene adducts of maleic anhydride formed onto at least monounsaturated carboxylic acids with a chain length of from 10 to 25 carbon atoms and acid numbers from 10 to 140, which are preferably buffered to pH values around 6.5 with amino and/or amido compounds, such as triethanolamine, or glycol esters of aspartic acid and of glutamic acid as a result of the formation of salt-like bonds.

Preparations with these solubility promoters, however, were not flowable and the deodorant solutions formulated therefrom tend toward clouding and precipitation of individual components even at very low water contents (cf. DE-A-40 14 055 page 2, lines 50–52).

One improvement is the solution proposed in the patent specification DE-B-40 14 055, in which the applicants describe compositions with deodorizing action, comprising the zinc salt of ricinoleic acid and/or the zinc salt of abetic acid and/or further zinc salts of other saturated or unsaturated hydroxylated fatty acids having 16 or more carbon atoms, and also 5 to 50%, by weight, of an ethoxylated fatty alcohol with straight or branched alkyl chain and a carbon number between 10 and 18 with fewer than 30 ethylene oxide units per molecule, and 5 to 30%, by weight, of a tertiary amine.

The tertiary amines disclosed in the '055 reference are tertiary amino alcohols, such as, for example, triethanolamine or N,N,N',N'-tetrakis(2-hydroxypropyl)ethylenediamine.

The amino alcohols present in the prior art do not represent any problem for technical applications where there is no skin contact. For use in applications with skin contact, such as, in cosmetic products, however, more and more alternatives to amino alcohols are desired since the amino alcohols often comprise impurities of secondary amines. In addition, amino alcohols have also received negative headline coverage due to sensitizing and allergic reactions upon their use on skin.

Although the prior art formulations do represent very good progress, there is still a need for further improvement. For instance, the solubility in water or dilutability with water of the formulations without additional mono- and polyhydric alcohols as solubility promoters has still not been satisfactorily achieved.

SUMMARY OF THE INVENTION

There is therefore still a need for improved formulations for zinc ricinoleate which, not only have a considerably improved solubility in water compared with the prior art and are thus able to improve the solubility of zinc ricinoleate in the deodorizing composition while maintaining it stably in solution even when the storage period is prolonged and the water content high, but are also based on raw materials which in cosmetology, due to their nonrisky and skin-friendly properties, are generally accepted and wherever possible also have a significant additional utility.

Such an additional utility is a positive factor since consumers expect deodorants, like other cosmetic products for bodycare, to have multiple or multifunctional properties. In addition to the deodorant action, for example, the positive effect on nutrient supply or else on regeneration of the skin may, for example, be of particular interest.

In addition to mildness and tolerability by the skin, an increased demand for alcohol-free products is also to be noted, since alcohol-containing formulations can, in many cases, lead to skin irritations.

These additional utilities are also of interest for the application area of domestic and industrial odors, since such systems are primarily aqueous, some of them also being further diluted. Through the choice of the auxiliaries used it is simultaneously possible to achieve better ecological compatibility of the deodorizing system.

Preferably, for this reason, formulations containing zinc ricinoleate should comprise those raw materials as solubility promoters which are nontoxic, are preferably of natural origin, are tolerated very readily by the skin, have high compatibility with other ingredients and can be incorporated into deodorants without problems. It is particularly desirable if these raw materials can additionally perform the function of certain components which have hitherto been used in deodorant applications, such as, for example, pH regulators, agents for calming the skin or preventing inflammation.

It is an object of the invention to provide such formulations with deodorizing action.

Surprisingly, it has been found that through the co-use of amino-functional amino acids, salts and/or derivatives thereof, compositions with deodorizing action are obtained which satisfy all of these desired criteria.

The invention therefore provides preparations with deodorizing action, comprising
a) the zinc salt of ricinoleic acid;
b) at least one amino-functional amino acid;
c) solubility promoters;
d) organic and/or inorganic acids; and
e) optionally, water.

The present invention further provides for uses of these preparations for the preparation of deodorizing hygienic and cosmetic formulations, deodorizing household cleaners, industrial cleaners, adsorbents in filters, deodorizing formulations for use in private and commercial animal keeping, deodorizing formulations for the treatment of textile fibers and fabrics.

DETAILED DESCRIPTION OF THE INVENTION

As stated above, the present invention provides preparations with deodorizing action which include the zinc salt of ricinoleic acid; at least one amino functional amino acid; at least one solubility promoter; and at least one organic and/or inorganic acid. The inventive preparations may further include water as an optional component.

The zinc salts of ricinoleic acid which can be co-used according to the present invention are products that are available commercially under the respective trade names, such as, in particular, TEGO® Sorb, TEGODEO® or ORTEGOL® 2000. These products are all commercially available from Goldschmidt AG.

The zinc salt of ricinoleic acid can be co-used in amounts of from 0.01 to 60%, by weight, preferably in amounts of from 20 to 60%, by weight, based on the active ingredient concentrate.

The amino-functional amino acids co-used according to the present invention are preferably lysine, hydroxylysine, arginine, and derivatives and salts thereof with organic or inorganic acids alone or in a mixture with one another or among one another. Small fractions of further natural or synthetic amino acids are also possible.

The use of amino acids as active ingredients in cosmetic applications is already widely described. Due to their zwitterionic nature, amino acids act as buffers and stabilize the acid protective mantle of the skin.

L-Arginine is a semi-essential amino acid which is produced naturally in the body and which has to be supplemented through nutrition in deficiency situations. It has a skin-moisturizing action and belongs to the natural moisturizing factors (NMF) of the skin. A deficiency of arginine is causally linked to a reduced urea content in the skin, since urea is a metabolic secondary product of arginine. As a result, the natural moisturizing gradient of the skin is impaired, possibly leading to phenomena such as dry skin, cracking and flaking. A review of trials with topically applied L-arginine is given by Wohlrab J, Marsch W Ch. in Z. Hautkr. 2000; 75: 485–486.

Lysine is one part of many proteins and correspondingly has many functions within the body. It contributes to growth, to tissue repair, to the formation of enzymes, hormones and antibodies, and also to the synthesis of collagen and bone health. Lysine possibly helps to absorb and store calcium. Lysine further maintains the nitrogen balance within the body and plays an important role in the immune system. Antiviral capabilities, for example, are also known.

Both through lysine and also arginine, it is possible to improve, to an extraordinary degree, the tolerability by the skin and mucosa of irritative substances.

According to a further embodiment of the present invention, the inventive preparations can also comprise derivatives of the amino-functional amino acids. These include arginine and lysine salts, in particular, those with long-chain fatty acids, which, due to their surface-active properties, act as mild, skin-friendly surfactants. Such materials are supplied commercially, for example, under the trade name "Aminosoap" from Ajinomoto. It is also possible to use N-acyl derivatives of lysine and arginine and cationically modified fatty-chemically modified variants thereof.

The amino-functional amino acids can be co-used in amounts of from 0.01 to 40%, by weight, preferably in amounts of from 0.1 to 30%, by weight, based on the overall formulation.

For the purposes of the present invention, solubility promoters include: nonionic and ionic surfactants, such as alkoxylates, polyglycerols, glycol ethers, glycols, polyethylene glycols, polypropylene glycols, polybutylene glycols, glycerol ester ethoxylates, polysorbates, alkyl ether sulfates, alkyl- and/or arylsulfonates, alkyl sulfates, ester sulfonates (sulfo-fatty acid esters), ligninsulfonates, fatty acid cyanamides, anionic sulfosuccinic acid surfactants, fatty acid isethionates, acylaminoalkane-sulfonates (fatty acid taurides), fatty acid sarcosinates, ether carboxylic acids and alkyl (ether)phosphates.

Preferred nonionic solubility promoters for use in the present invention are the $C_2$–$C_6$-alkylene glycols and poly-$C_2$–$C_3$-alkylene glycol ethers, optionally, etherified on one side with a $C_1$–$C_6$-alkanol and having, on average, 1 to 9 identical or different, preferably identical, alkylene glycol groups per molecule, and also alcohols and fatty alcohol polyglycol ethers, preferably propylene glycol, dipropylene glycol, trimethylolpropane, and fatty alcohols with low degrees of ethoxylation having 6 to 22, preferably 8 to 18, more preferably 8 to 12, and even more preferably 8 to 11, carbon atoms.

Preferred ionic solubility promoters are alkyl ether sulfates, sulfosuccinic acid surfactants, polyacrylates and phosphonic acids, preferably lauryl sulfate, lauryl ether sulfate, sodium sulfosuccinic acid diisooctyl ester, 1-hydroxyethane-1, 1-diphosphonic acid, and diacetyltartaric esters.

The solubility promoters can be co-used in amounts of from 0.01 to 40%, by weight, preferably in amounts of from 0.1 to 30%, by weight, based on the overall formulation.

The organic and/or inorganic acids used in the present invention are, in particular, HCl, phosphoric acid, acetic acid, lactic acid and/or citric acid. The amount used is essentially dependent on the type and the amount of the co-used amino acid and should, in any case, suffice to adjust the pH of the overall formulation from about 3 to 9. Amounts of from 0.01 to 10%, by weight, are generally sufficient for this purpose.

The auxiliaries and additives used in the present invention are products which are known in the respective field of use, predominantly CTFA listed, in customary amounts.

The water used may be demineralized water or, alternatively tap water may be used, preferably tap water with degrees of hardness which are not too high.

The compositions according to the present invention can be prepared by mixing the components in the customary manner, such as, for example, by simultaneous, portionwise or successive addition of amino acid and organic acid to an initial charge of intensively stirred and, optionally, heated solubility promoter, and the subsequent metered addition of the further optionally co-used components.

The active ingredient combinations according to the present invention can, like the known zinc ricinoleates available on the market, be incorporated into all customary deodorant formulations. These include: pump spray solutions, liquid soaps, deodorant sprays and deodorant creams. It is also possible to add the corresponding formulations to other customarily used cosmetic products, such as, for example, hair shampoos or hair rinses, provided known incompatibilities do not exclude this from the outset.

These active ingredient combinations can also be used in cleaning formulations, such as, for example, in hand dishwashing detergents, all-purpose cleaners, carpet cleaners, deowipes or as air freshener, deodorizing household cleaners, industrial cleaners, adsorbents in filters, deodorizing formulations for use in domestic and commercial animal keeping, deodorizing formulations for the treatment of textile fibers and fabrics.

The additional use of alcohols in particular ethanol, or isopropyl alcohol, is possible and should not be excluded a priori since such additives can be co-used, from esthetic and also preservative points of view, wherever no skin irritations have to be feared.

It was, however, entirely surprising that, by using the inventive active ingredient combinations, it is also possible to prepare stable, alcohol-free deodorant formulations which do not precipitate out in dilute, aqueous solutions, thereby being deactivated.

The deodorants according to the present invention, their preparation and use are illustrated in more detail in the examples below. The chemical characterization of the trade names mentioned in the examples is given in Table 1.

TABLE 1

| Product name | Manufacturer | INCI name/chemical description |
| --- | --- | --- |
| Tego ® SMO 80 | Goldschmidt | Polysorbate 80 |
| Tego ® Alkanol L23P | Goldschmidt | Laureth-23 |
| Renex ® 30 | Uniqema | Trideceth-12 |
| Varonic ® APM | Goldschmidt | PPG-3 Myristyl Ether |
| Tagat ® O2 | Goldschmidt | PEG-20 Glyceryl Oleate |
| Tego ® SML 20 | Goldschmidt | Polysorbate 20 |
| Neutrol ® TE | BASF | N,N,N',N'-Tetrakis(2-hydroxypropyl)ethylenediamine |
| Dehydol ® LS 3 | Henkel | Laureth-3 |
| TEGO ® SORB PY 88 TQ | Goldschmidt | Zinc ricinoleate |
| TEGODEO ® PY 88 TQ | Goldschmidt | Zinc ricinoleate |
| TEGO ® SORB Conc. 50 | Goldschmidt | Zinc ricinoleate; Tetrahydroxypropylethylenediamine; Laureth-3; Propylene glycol |
| TEGOTEN ® S EC 11 | Goldschmidt | End-capped Fatty Alcohol Ethoxylate |
| IMBENTIN ® U 050 | Kolb | Fatty alcohol polyethylene glycol ether |
| IMBENTIN ® AG 100/040 | Kolb | Fatty alcohol polyethylene glycol ether |
| IMBENTIN ® AG 810/050 | Kolb | Fatty alcohol polyethylene glycol ether |
| DATAMULS ® 43 | Goldschmidt | Diacetyltartaric ester |
| REWOPOL ® SB FA 30 | Goldschmidt | Disodium Laureth Sulfosuccinate |
| REWOPOL ® SB DO 75 | Goldschmidt | Di-Isooctyl Sulfosuccinate |
| SEQUION ® 40 Na 32 | Polygon | Sodium Diethylenetriamine Pentamethylene Phosphonate |
| TEXAPON ® NSO | Cognis | Sodium Laureth Sulfate |
| TEXAPON ® K 12 | Cognis | Sodium Lauryl Sulfate |
| HEDP, Dequest 2016 | Monsanto | 1-Hydroxyethane-1,1-Diphosphonic acid, Sodium Salt |
| Sequion MS 84 | Polygon | Polyacrylic acid, Na Salt |
| Sokalan PA 20 | BASF | Polyacrylic acid, Na Salt |
| REWOPOL ® S 2311 | Goldschmidt | Mixture of Sodium Dodecylbenzenesulfonate, Sodium Laureth sulfate, Laureth-10 and Cocamide-DEA |

TABLE 1-continued

| Product name | Manufacturer | INCI name/chemical description |
|---|---|---|
| REWOPOL ® HM 28 | Goldschmidt | Mixture of Sodium Laureth Sulfate, Disodium Sulfosuccinate and Cocamide-DEA |
| REWOPOL ® TS 35 | Goldschmidt | Mixture of Lauryl sulfate, Disodium Lauramido MEA Sulfosuccinate and Disodium Cocamido MEA Sulfosuccinate |
| REWOPOL ® TS SP 25 | Goldschmidt | Mixture of Sodium Isooctyl Sulfate, Di-isooctyl Sulfosuccinate, Sodium Xylenesulfonate, Polystyrene and Defoamer |

EXAMPLE 15

The experiments below describe preferred compositions (K-1 to K-13) of the active ingredient concentrates according to the present invention. The compositions are made utilizing the procedure described in the present invention. K—0 is a comparative composition. The compositions were adjusted to a pH of 8 or 7 using a 50% solution of citric acid. Table 2 also describes the appearance of the compositions K-0 to K-13 at room temperature (RT), at 40° C. and at 5° C.

TABLE 2

| Examples: | K-0 | K-1 | K-2 | K-3 | K-4 | K-5 | K-6 | K-7 | K-8 | K-9 | K-10 | K-11 | K-12 | K-13 |
|---|---|---|---|---|---|---|---|---|---|---|---|---|---|---|
| Zinc ricinoleate (TEGODEO ® PY 88 TQ) | 50 | 40 | 30 | 30 | 25 | 24 | 23 | 20 | 20 | — | — | — | — | — |
| Zinc ricinoleate (TEGO ® Sorb PY 88 TQ) | — | — | — | — | — | — | — | — | — | 30 | 50 | 50 | 50 | 30 |
| Lysine | — | 15 | 25 | 25 | — | 27 | 23.5 | — | 25 | — | — | — | — | — |
| Arginine | — | — | — | — | 30 | — | — | 25 | — | 10 | 10.5 | 10.5 | 10.5 | 10.5 |
| Neutral ® TE | 15 | — | — | — | — | — | — | — | — | — | 9.5 | 9.5 | 9.5 | — |
| Datamuls ® 43 | — | — | — | — | — | — | — | — | — | 3 | 3 | 3 | 3 | 3 |
| Dequest ® 2016 | — | — | — | — | — | — | — | — | — | 17 | — | — | — | 18 |
| REWOPOL ® SB DO 75 | — | — | — | — | — | — | — | — | — | — | — | — | — | 2 |
| Dehydol ® LS 3 | 30 | — | — | — | — | — | — | — | — | — | — | — | — | — |
| TEGOTENS ® EC 11 | — | — | — | — | — | — | — | — | — | — | 5 | — | — | — |
| Imbentin ® U 050 | — | — | — | — | — | — | — | — | — | — | — | 5 | — | — |
| Imbentin ® AG 100/040 | — | — | — | — | — | — | — | — | — | 5 | — | — | — | — |
| Imbentin ® AG 810/050 | — | — | — | — | — | — | — | — | — | — | — | — | 5 | 5 |
| Propylene glycol | 5 | 22.5 | — | 20 | 30 | 33 | 30 | 30 | 30 | — | — | — | — | — |
| Dipropylene glycol | — | — | 20 | — | — | — | — | — | — | — | — | — | — | — |
| Water | — | 22.5 | 25 | 25 | 15 | 16 | 23.5 | 25 | 25 | 35 | 22 | 22 | 22 | 36.5 |
| PH | | Mixtures were adjusted to a pH of 8 with 50% strength citric acid solution | | | | | | | | 7 | 7 | 7 | 7 | 7 |
| Appearance at RT | HC | Cl | 2P | HC | HC | HC | HC | HC | HC | HC | HC | HC | HC | HC |
| Appearance at 40° C. | HC | | | HC | HC | HC | HC | HC | HC | HC | HC | HC | HC | HC |
| Appearance at 5° C. | HC | | | HC | HC | P | P | HC | HC | HC | HC | HC | HC | HC |

H = Homogeneous
C = Clear
Cl = Cloudy
2P = 2 Phases
P = Precipitation

The better water compatibility of the compositions according to the present invention with deodorizing action will be demonstrated by reference to the examples of pump spray formulations shown in Table 3 below.

TABLE 3

| Application Example | C-1 | C-2 | A-3 | A-4 | A-5 | A-6 | A-7 | A-8 | A-9 | A-10 | A-11 | A-12 |
|---|---|---|---|---|---|---|---|---|---|---|---|---|
| Comparative Example K-0 | 2.0 | 2.0 | — | — | — | — | — | — | — | — | — | — |
| Example K-3 | — | — | — | 3.4 | 3.4 | — | — | — | — | — | — | — |
| Example K-6 | — | — | — | — | — | — | — | 5 | 5 | 5 | 5 | 5 |
| Example K-7 | — | — | 5.0 | — | — | — | — | — | — | — | — | — |
| Example K-8 | — | — | — | — | — | 5 | 5 | — | — | — | — | — |
| Tego ® SMO 80 | 3.5 | 3.5 | 12.5 | 10 | 14 | 10 | 12 | 12.5 | — | — | — | — |

TABLE 3-continued

| Application Example | C-1 | C-2 | A-3 | A-4 | A-5 | A-6 | A-7 | A-8 | A-9 | A-10 | A-11 | A-12 |
|---|---|---|---|---|---|---|---|---|---|---|---|---|
| Tego ® Alkanol L23P | — | — | — | — | — | — | — | — | 7.5 | — | — | — |
| Renex ® 30 | — | — | — | — | — | — | — | — | — | 5 | — | — |
| Tagat ® O2 | — | — | — | — | — | — | — | — | — | — | 12.5 | — |
| Tego ® SML 20 | — | — | — | — | — | — | — | — | — | — | — | 10 |
| Triethanolamine | 0.5 | 0.5 | — | — | — | — | — | — | — | — | — | — |
| Dipropylene glycol | — | — | 4.0 | 4.0 | 4.0 | 4.0 | 4.0 | 4.0 | 4.0 | 4.0 | 4.0 | 4.0 |
| SD Alcohol 39C | 33 | — | — | 32 | — | 32 | — | — | — | — | — | — |
| Perfume | — | — | 0.9 | 0.9 | 0.9 | 0.9 | 0.9 | 0.9 | 0.5 | 0.9 | 0.9 | 0.5 |
| Water | 60 | 93 | 77.6 | 49.7 | 77.7 | 48.1 | 78.1 | 77.6 | 83 | 85.1 | 77.6 | 80.5 |
| Lactic acid | 1 | 1 | — | — | — | — | — | — | — | — | — | — |
| Zn ricinoleate content | 1 | 1 | 1 | 1 | 1 | 1 | 1 | 1.15 | 1.15 | 1.15 | 1.15 | 1.15 |

All of the pump spray solutions were adjusted to a pH of 5.5 with 50% strength citric acid solution. In all of the cases according to the present invention, clear solutions were obtained after mixing which remained clear even after storage for 3 months at temperatures of 40° C. and 10 thaw-freeze cycles. The solutions prepared with Comparative Example K-0 become cloudy at room temperature, and precipitations resulted.

Using Example K-6, a deodorant stick was developed. The stick formulation is shown in Table 4

TABLE 4

Stick formulation

|  | Example A-13 |
|---|---|
| Varonic ® APM | 70.5 |
| Na stearate | 8.0 |
| Propylene glycol | 10.0 |
| Water | 3.0 |

TABLE 4-continued

Stick formulation

|  | Example A-13 |
|---|---|
| Perfume | 1.0 |
| Example K-6 | 7.5 |
| Zn ricinoleate content | 1.7 |

This formulation was stable after 3 months at 40° C. and 10 thaw-freeze cycles.

For use in cleaning solutions, better water compatibility and reduced residue formation on hard surfaces play an important role. Examples of nondilutable cleaners compared to the examples according to the present invention (see table 5), which are characterized by a higher active ingredient content, serve to emphasize the differences.

TABLE 5

| Application Example | C-3 | C-4 | V-5 | V-6 | A-14 | A-15 | A-16 | A-17 | A-18 | A-19 | A-20 | A-21 |
|---|---|---|---|---|---|---|---|---|---|---|---|---|
| Comparative Example K-0 | 1.0 | 1.0 | 1.0 | 2.0 | — | — | — | — | — | — | — | — |
| Example K-12 | — | — | — | — | 1.0 | 3.0 | 3.0 | 15.0 | 10.0 | 8.0 | 8.0 | 15.0 |
| REWOPOL ® SB FA 30 | 6.0 | — | — | — | 6.0 | 6.0 | — | — | — | — | — | — |
| TEGOTENS ® DO | — | 6.0 | — | — | — | — | — | — | — | — | — | — |
| TEGOTENS ® B 810 | — | — | 6.0 | — | — | — | — | — | — | — | — | — |
| TEGOTENS ® 485 | — | — | — | 15.0 | — | — | — | — | — | — | — | — |
| TEXAPON ® K12 | — | — | — | — | — | — | — | — | — | 10.0 | — | 10.0 |
| TEXAPON ® NSO | — | — | — | — | — | — | 10.0 | 10.0 | 10.0 | — | 10.0 | — |
| Sokalan ® PA 20 | — | — | — | — | — | — | — | — | — | — | 5.0 | — |
| Sequion ® MS 84 | — | — | — | — | — | — | — | — | 2.5 | — | — | — |
| Sequion ® 40 Na 32 | 2.5 | — | — | — | 1.0 | 2.5 | 2.5 | — | — | — | — | — |
| Dequest ® 2016 | — | — | — | — | — | — | — | 2.5 | — | 2.5 | — | 2.5 |
| Triethanolamine | 0.6 | 0.6 | 0.6 | — | — | — | — | — | — | — | — | — |
| Lactic acid | 0.6 | 0.6 | 0.6 | — | — | — | — | — | — | — | — | — |
| Water | 89.3 | 91.8 | 91.8 | 83.0 | 92.0 | 88.5 | 84.5 | 72.5 | 77.5 | 89.5 | 87.0 | 72.5 |
| Zn ricinoleate content | 0.5 | 0.5 | 0.5 | 1 | 0.5 | 1.5 | 1.5 | 7.5 | 5.0 | 4.0 | 4.0 | 7.5 |
|  | C-3 | C-4 | C-5 | C-6 | A-14 | A-15 | A-16 | A-17 | A-18 | A-19 | A-20 | A-21 |
| Appearance at RT after Storage for 3 months | HC | HC | HC | HC | HC | HC | HC | HC | HC | HC | HC | HC |
| PH | 6 | 6 | 6 | 7 | 7 | 7 | 8 | 8 | 8 | 8 | 8 | 8 |

H = Homogeneous
C = Clear
P = Precipitations
Cl = Cloudy

Processing in cleaner concentrates (see Table 6) was checked in order to document easier incorporation into known surfactant systems. The surfactant systems used are concentrates for the simple preparation of the respective fields of use.

TABLE 6

| Application Example | A-22 | A-23 | A-24 | A-25 | A-26 | A-27 | A-28 | A-29 | A-30 | A-31 | A-32 | A-33 |
|---|---|---|---|---|---|---|---|---|---|---|---|---|
| Intended use | All-purpose cleaner | | | Hand dishwashing detergent | | | Carpet/upholstery foam cleaner | | | Carpet/upholstery spray extraction | | |
| Example K-12 | 1.0 | 3.0 | 5.0 | 1.0 | 3.0 | 5.0 | 1.0 | 3.0 | 5.0 | 1.0 | 3.0 | 5.0 |
| REWOPOL ® S 2311 | 50.0 | 50.0 | 50.0 | — | — | — | — | — | — | — | — | — |
| REWOPOL ® HM 28 | — | — | — | 50.0 | 50.0 | 50.0 | — | — | — | — | — | — |
| REWOPOL ® TS 35 | — | — | — | — | — | — | 50.0 | 50.0 | 50.0 | — | — | — |
| REWOPOL ® TS SP 25 | — | — | — | — | — | — | — | — | — | 50.0 | 50.0 | 50.0 |
| Water | 49.0 | 47.0 | 45.0 | 49.0 | 47.0 | 45.0 | 49.0 | 47.0 | 45.0 | 49.0 | 47.0 | 45.0 |
| Zn ricinoleate content | 0.5 | 1.5 | 2.5 | 0.5 | 1.5 | 2.5 | 0.5 | 1.5 | 2.5 | 0.5 | 1.5 | 2.5 |
| Appearance at RT after storage for 3 months | HC | HC | HC | HC | HC | HC | HC | HC | P | H | H | H |

H = Homogeneous
C = Clear
Cl = Cloudy
P = Precipitation

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A preparation with deodorizing action consisting essentially of:
    0.01 to 60%, by weight, of a zinc salt of ricinoleic acid;
    0.01 to 40%, by weight, of a single amino-functional amino acid;
    0.01 to 40%, by weight, of at least one solubility promoter; and
    0.01 to 10%, by weight, of at least one organic acid, inorganic acid or mixtures thereof.

2. The preparation with deodorizing action of claim 1 further comprising water to 100%, by weight.

3. The preparation with deodorizing action of claim 1 wherein said amino-functional amino acid comprises lysine, hydroxylysine, arginine, derivatives or salts thereof.

4. The preparation with deodorizing action of claim 1 wherein said at least one solubility promoter is an ionic surfactant, a nonionic surfactant, a glycol or mixtures thereof.

5. The preparation with deodorizing action of claim 1 wherein said organic acid is acetic acid, lactic acid, citric acid or mixtures thereof.

6. A formulation comprising at least a preparation consisting essentially of
    0.01 to 60%, by weight, of a zinc salt of ricinoleic acid;
    0.01 to 40%, by weight, of a single amino-functional amino acid;
    0.01 to 40%, by weight, of at least one solubility promoter; and
    0.01 to 10%, by weight, of at least one organic acid, inorganic acid or mixtures thereof.

7. The formulation of claim 6 further comprising hygienic ingredients.

8. The formulation of claim 6 further comprising cosmetic ingredients.

9. A deodorant comprising at least the preparation of claim 1.

* * * * *